(12) United States Patent
McKinnon et al.

(10) Patent No.: US 6,190,326 B1
(45) Date of Patent: Feb. 20, 2001

(54) METHOD AND APPARATUS FOR OBTAINING PATIENT RESPIRATORY DATA

(75) Inventors: Robert J. McKinnon, Highlands Ranch, CO (US); Patrick L. Riley, Salt Lake City, UT (US); James L. Wolf, Conifer, CO (US)

(73) Assignee: Medtrac Technologies, Inc., Lakewood, CO (US)

( * ) Notice: Under 35 U.S.C. 154(b), the term of this patent shall be extended for 0 days.

(21) Appl. No.: 09/299,195

(22) Filed: Apr. 23, 1999

(51) Int. Cl.[7] ....................................... A61B 5/08
(52) U.S. Cl. ..................... 600/529; 600/300; 600/532; 128/200.24
(58) Field of Search .................... 600/300, 529, 600/532, 538; 128/200.24, 200.26

(56) References Cited

U.S. PATENT DOCUMENTS

| 5,518,002 | 5/1996 | Wolf et al. ........................ 128/725 |
| 5,606,976 | 3/1997 | Marshall et al. .................. 128/723 |
| 5,623,938 | 4/1997 | Addiss ............................. 128/723 |
| 5,626,144 | 5/1997 | Tacklind et al. ................. 128/725 |

*Primary Examiner*—Cary O'Connor
*Assistant Examiner*—Ryan Carter
(74) *Attorney, Agent, or Firm*—Sheridan Ross P.C.

(57) ABSTRACT

A system for collecting patient respiratory information includes a base unit and a removable mouthpiece unit. The mouthpiece unit includes sensors that sense parameters of a patient's breath when the patient blows into the mouthpiece unit. The base unit receives and processes the information from the mouthpiece unit and stores it in chronological fashion for later analysis by a physician. The mouthpiece unit includes a memory for storing identification information for a patient who has been assigned the mouthpiece unit. When the mouthpiece unit is inserted into the base unit, the base unit reads the identification information from the mouthpiece unit and stores all measurement information in association therewith. In this manner, a single base unit can be used to collect information for a plurality of different patients without creating confusion as to which measurement results correspond to which patients. A cable assembly can be disposed intermediate the mouthpiece unit and the base unit to allow the patient to view a display on the base unit while simultaneously exhaling into the mouthpiece unit.

29 Claims, 10 Drawing Sheets

METHOD AND APPARATUS FOR OBTAINING PATIENT RESPIRATORY DATA

FIELD OF THE INVENTION

The invention relates generally to medical devices and, more specifically, to devices for measuring and logging patient respiratory information.

BACKGROUND OF THE INVENTION

Respiratory problems are relatively common in society today. For example, some estimate that nearly 5% of the population of the United States suffer from asthma. Effective treatment of respiratory conditions can be complicated, sometimes requiring continuous monitoring and recording of respiratory function and symptoms in conjunction with controlled application of medication to bring a condition under control. In such cases, a physician will generally review the recorded data for a particular patient to determine how the patient is reacting to a prescribed treatment plan and make modifications to the treatment plan based thereon. Over time, a treatment regimen is developed that stabilizes the patient's condition to allow normal daily functioning without fear of life threatening attacks or the like.

As can be appreciated, the procedures for monitoring and recording respiratory function and the use of medicines can be complicated and time consuming. Much of the responsibility for maintaining accurate records of respiratory function and administration of medication falls upon the patient, who must then report recorded information to the physician. In many cases, this information gathering task proves to be overly burdensome for a patient untrained in such matters, resulting in incomplete, inconsistent, and/or inaccurate data collection. This data is then made available to the attending physician, who uses it to determine whether adjustments need to be made in the patient's treatment regimen. Because the information being used by the physician is sketchy at best, the physician's ability to make the correct treatment decisions is compromised and an optimal treatment regimen takes longer to develop.

Therefore, a need exists for a method and apparatus for accurately collecting information about a patient's respiratory condition from the patient. The method and apparatus will preferably be simple and straightforward to use, highly reliable, and relatively automatic.

SUMMARY OF THE INVENTION

The present invention relates to a system that is capable of accurately collecting and recording patient respiratory information for use, for example, in developing/modifying a treatment regimen for the patient. The system includes both measurement functionality for measuring the patient's present respiratory condition and storage functionality for storing and organizing the measured information. In addition, the system includes patient management functionality for managing the activity of the patient to ensure that, for example, measurements are made at the appropriate times and in accordance with the physician's instructions. For example, the patient management functionality can prompt the patient when it is time to take an appropriate respiratory reading and also coach the patient during the reading to increase the likelihood of proper performance. Measurement results are then recorded by the patient management functionality with corresponding time/date information for later transmittal to the physician. In one embodiment, the system is capable of communicating with one or more medication dispensing apparatuses for obtaining confirmation that an appropriate dosage of medicine was actually administered by the patient at a particular time and in a proper fashion. As with the other information, this information is also stored by the system and eventually transferred to the physician.

In a preferred embodiment, the system includes a base unit that includes the intelligence for performing the management, measurement, and storage functions. That is, the base unit includes at least one processor that is programmed to perform the noted functions in conjunction with input/actions by the patient. In addition, the system includes at least one detachable mouthpiece unit for insertion into the base unit when a measurement is to be performed. The mouthpiece unit includes the sensors that are required for sensing respiratory function related parameters from a patient's breath when the patient blows, or possibly inhales during some of the times, into the mouthpiece unit. When the mouthpiece unit is attached to the base unit, the sensors are able to deliver raw measurement data to the measurement functionality within the base unit for processing. After the information has been processed, the measurement results are stored within the base unit for later review by a physician. The measurement results can also be displayed to the patient on a display of the base unit along with any relevant treatment suggestions.

In accordance with one aspect of the present invention, each detachable mouthpiece unit includes an internal memory for storing, among other things, identification information identifying a patient having exclusive use of that mouthpiece unit. When the mouthpiece unit is inserted into the base unit, the identification information stored in the mouthpiece unit is transferred to the base unit which stores the identification information in its internal memory. Results of all subsequent tests performed by the base unit using that inserted mouthpiece unit are then stored within the base unit in association with the identified patient. In this manner, multiple patients, each having their own dedicated mouthpiece unit, can make use of a single base unit without confusion as to which respiratory-related information corresponds to which patient. In addition, because each patient uses an entirely different mouthpiece unit, concerns about possible contamination within the system are significantly reduced.

DETAILED DESCRIPTION

Figure 1:
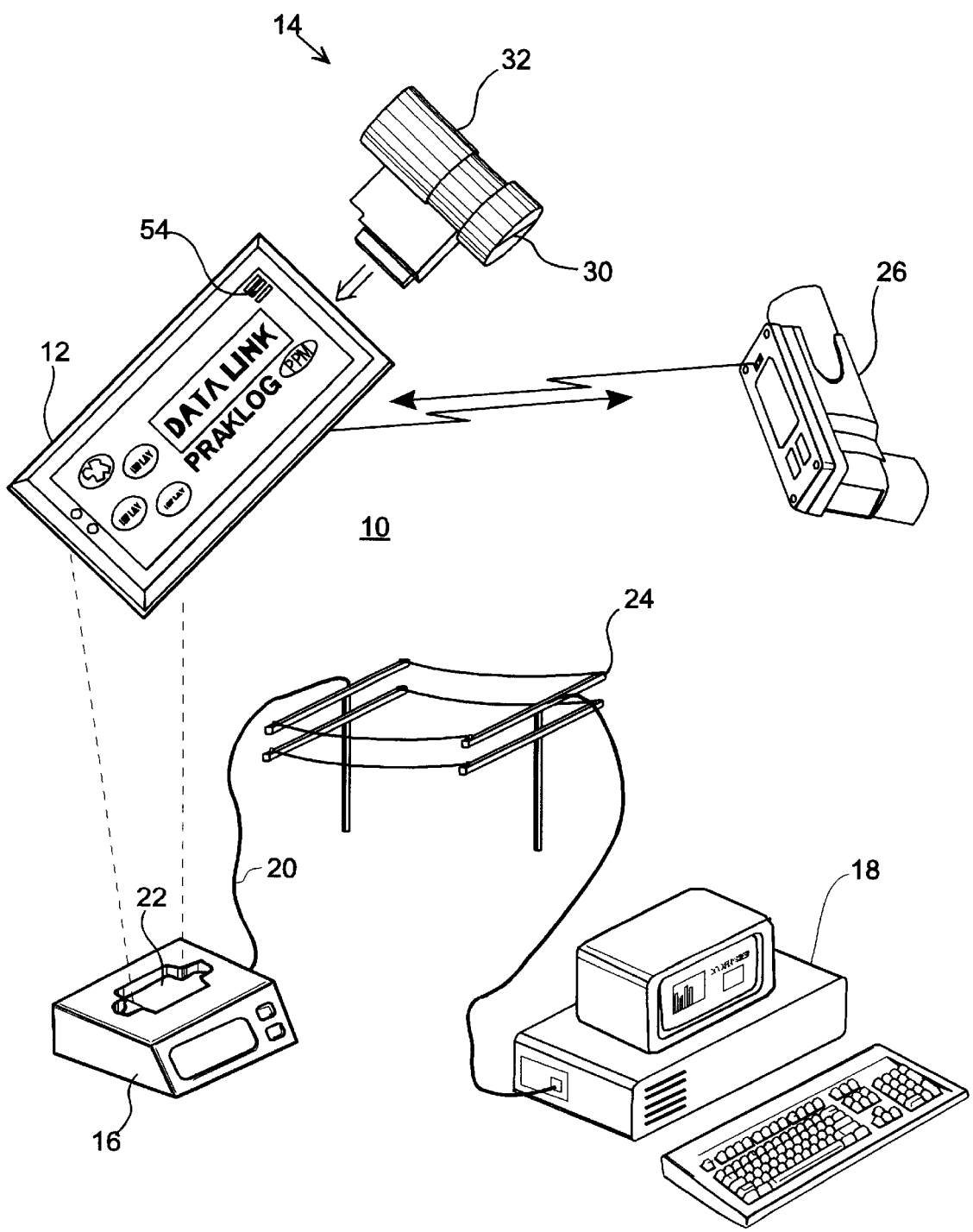
FIG. 1 is a diagram illustrating a system in accordance with one embodiment of the present invention.

FIG. 1 is a diagram illustrating a system 10 in accordance with one embodiment of the present invention. As illustrated, the system 10 includes: a portable base unit 12, a detachable mouthpiece unit or device 14 which can be removably coupled to the portable base unit 12, a docking station 16, and a physician data collection station 18. The portable base unit 12 includes the measurement and storage functionality that is used to collect and record respiratory related information for the patient. The mouthpiece unit 14 plugs into the base unit 12 and includes an air flow chamber 32 having an orifice 30 for receiving a patient's breath during a test. Sensors within the air flow chamber 32 measure raw parameters of the patient's breath which are then converted to meaningful test results within the base unit 12. The docking station 16 is used to, among other things, transfer the collected data from the base unit 12 to the physician data collection station 18 for analysis by the patient's physician.

The portable base unit 12 can be carried by a patient for use in collecting and storing respiratory-related information about the patient as the patient goes about his ordinary daily routine. Alternatively, the base unit 12 can be used in a multiple patient environment, such as a hospital or a home having two or more respiratory patients, to collect data from a number of different patients. As will be described in greater detail, the base unit 12 includes means for interacting with a patient to ensure that, for example, measurements are taken at appropriate times and in an appropriate manner (i.e., in accordance with the physician's instructions). When a measurement is to be taken, the patient inserts the mouthpiece unit 14 (if it isn't already inserted) into the base unit 12 and, after an appropriate signal from the base unit 12, blows into the orifice 30 in the air flow chamber 32 of the mouthpiece unit 14. The sensors within the mouthpiece unit 14 extract raw data from the patient's breath and deliver the raw measurement data to processing circuitry within the base unit 12 to generate the measurement results. The measurement data is then stored within the base unit 12 for future use.

As shown in FIG. 1, the portable base unit 12 also includes the ability to wirelessly communicate with peripheral devices, such as medication dispensing device 26, for use in tracking the timing and dosage levels of medications administered to the patient. In some cases, the base unit 12 will even be able to determine whether the medication dispensing device 26 was properly used by the patient (e.g., whether the patient inhaled the medication too fast, etc.). As with the respiratory measurement information, this information is also stored within the base unit 12 for future use.

As mentioned above, the docking station 16 is used to transfer the data collected by the base unit 12 to a physician data collection station 18 for analysis by a physician. The docking station 16 communicates with the physician data collection station 18 through a communication path 20 between the two units. The communication path 20 can include virtually any form of communication connection, either wired or wireless. For example, in one embodiment, a hardwired link (e.g., a coaxial cable) between the units is implemented. Alternatively, some form of communication network can be used to provide the required communication. In the illustrated embodiment, for example, a public switched telephone network (PSTN) 24 is used to establish a connection between the docking station 16 and the physician data collection station 18. Other networks, such as those including satellite links, cable television links, Internet links, terrestrial wireless links, optical fiber links, local area network (LAN) links, and the like can also be used in accordance with the present invention.

The docking station 16 includes a cradle 22 for insertion of the base unit 12 to permit the performance of various functions. For example, the cradle 22 includes data interface functionality for use in transferring data between the base unit 12 and the docking station 16. In addition, the cradle 22 can include structures for allowing the docking station 16 to charge the batteries of the base unit 12. After the base unit 12 has been inserted into the cradle 22, a user (e.g., the patient) instructs the docking station 16, using front panel controls on the docking station 16, to initiate a data transfer for an identified patient. The docking station 16 reads the data stored in the base unit 12 for the identified patient and stores it within an internal memory. The stored data is then transferred to the physician data collection station 18 via communication path 20 at an appropriate time.

After the respiratory-related data has been transferred to the docking station 16, it does not have to be immediately transferred to the physician data collection station 18. For example, the docking station 16 can be programmed to make transfers at regularly scheduled times. Alternatively, the docking station 16 can be programmed to automatically initiate a transfer when a predetermined amount of data has been collected from one or more patients. In another approach, the docking station 16 can be programmed to wait for the physician data collection station 18 to initiate the data transfer. In one embodiment, the docking station 16 is programmed to make all transfers in a default manner unless overridden during a particular session using the front panel controls.

The physician data collection station 18 is a device used by a physician to retrieve and organize respiratory information about his patients. Typically, the physician data collection station 18 will be a desk top personal computer used by the physician to perform and organize his daily practice. After a patient's respiratory-related information has been transferred to the physician data collection station 18, the physician analyzes the information to determine the patient's condition. As part of the analysis, the physician will generally check to see whether the patient has been properly following the physician's treatment instructions and, if so, to determine whether the treatment is producing the desired results. If the prescribed treatment is not producing the desired results, the physician can develop a modified treatment routine for the patient. If the information received by the physician indicates potential problems, the physician can call the patient directly and suggest that he come in for an office visit.

If the physician develops a modified treatment regimen for a patient, the base unit 12 used by the patient needs to be updated with the new treatment information. In a preferred embodiment of the invention, this is accomplished by delivering the modified treatment information back to the docking station 16, via the communication path 20, where it is stored in the internal memory of the docking station 16. If the corresponding base unit 12 is still docked within the docking station 16, the docking station 16 will immediately transfer the revised treatment information to the base unit 12 for use by the patient. Otherwise, the docking station 16 will hold the information in its internal memory until the appropriate base unit 12 is re-inserted. Alternatively, the physician can call the patient and request that he bring his base unit 12 to the physician's office for reprogramming.

Figure 2:
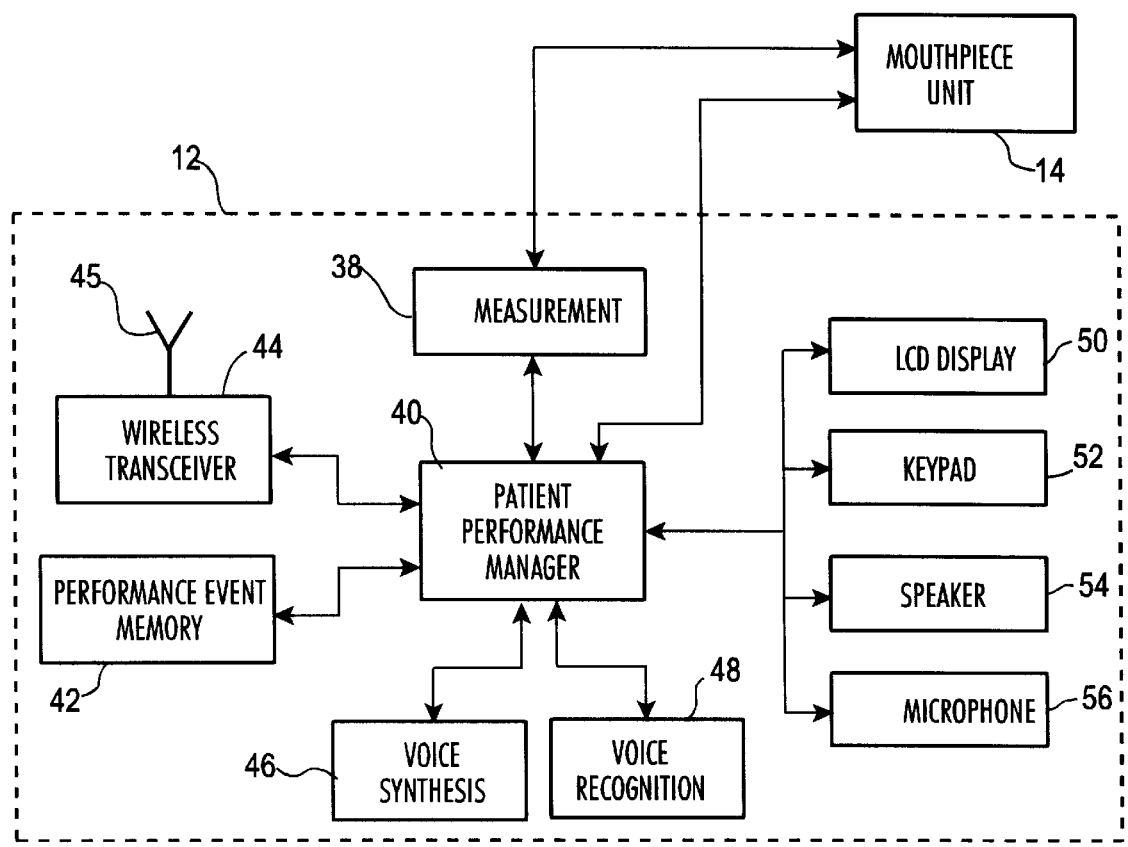
FIG. 2 is a block diagram illustrating functionality within a base unit in accordance with the present invention.

FIG. 2 is a block diagram illustrating the functionality within a base unit 12 in accordance with one embodiment of the present invention. It should be appreciated that the blocks illustrated in FIG. 2 (and other block diagrams referred to herein) represent functional elements that do not necessarily correspond to discrete hardware units. For example, in one embodiment of the present invention, the functions associated with multiple blocks in FIG. 2 are performed within a single digital processing device. Alternatively, multiple processing devices can be used to perform different functions. Virtually any type of digital processing device can be used within the base unit 12, including, for example, a general purpose microprocessor, a digital signal processor, a reduced instruction set computer, or a complex instruction set computer. Because the portable base unit 12 is battery powered, processors capable of low power operation are preferred.

As illustrated, the base unit 12 includes: a measurement unit 38, a patient performance manager (PPM) 40, a performance event memory 42, a wireless transceiver 44 coupled to a transducer 45, a voice synthesis unit 46, a voice recognition unit 48, a liquid crystal display (LCD) 50, a keypad 52, a speaker 54, and a microphone 56. The PPM 40 is operative for managing the activities of a patient associated with the base unit 12 in accordance with a treatment plan developed by the patient's physician. The specifics of the treatment plan are programmed into the PPM 40 by the physician either at the physician's office or remotely via, for example, the PSTN 24. The PPM 40 interacts with the patient using the LCD display 50, the keypad 52, the speaker 54, and/or the microphone 56 to ensure that the patient acts in accordance with the treatment regimen. For example, the PPM 40 can prompt the patient using the LCD display 50 or the speaker 54 when it is time to take a respiratory reading. Likewise, the PPM 40 can query the patient with respect to any symptoms the patient may be experiencing at a particular time. The PPM 40 then records the patient's activities/responses in the performance event memory 42 in a chronological fashion. In one embodiment, all entries stored in the performance event memory 42 are time tagged with both date and time-of-day so that an accurate time record is maintained of the patient's activities.

When a respiratory measurement is to be performed, the PPM 40 first checks to determine whether a detachable mouthpiece unit 14 is currently installed. If not, the patient is prompted using the speaker 54 and/or the LCD display 50 to insert the mouthpiece unit 14. When the PPM 40 determines that a mouthpiece unit 14 has been installed, it enables the measurement unit 38 to receive and process raw data from the detachable mouthpiece unit 14. The PPM 40 then prompts the patient to blow into the mouthpiece unit 14 in an appropriate manner. After the raw data has been processed in the measurement unit 38, the PPM 40 stores the results of the processing in the performance event memory 42 as described above. The PPM 40 can also display the results of the processing to the patient using the LCD display 50 along with further instruction or recommendations. Typical measurements include peak expiratory flow rate (PEFR), forced expiratory volume (FEV), expiratory temperature, forced vital capacity (FVC), forced expiratory volume—one second ($FEV_1$), forced expiratory volume—six seconds ($FEV_6$), forced vital capacity—six seconds ($FVC_6$), peak expiratory flow (PEF), forced expiratory flow—25%–75% ($FEF_{25\%-75\%}$), forced expiratory time—percentage (FET%), forced expiratory volume/forced vital capacity ratio ($FEV_1$/FVC Ratio), forced inspiratory vital capacity (FIVC) and expiratory curve.

As described previously, in one aspect of the present invention, the mouthpiece unit 14 includes an internal memory for storing, among other things, identification information identifying a patient associated with the mouthpiece unit 14. When such a mouthpiece unit 14 is inserted into the base unit 12, the PPM 40 reads the identification information to determine which patient the mouthpiece unit 14 belongs to. The PPM 40 then stores the results of all measurements made using that mouthpiece unit 14 in the performance event memory 42 in association with the identified patient. In this manner, the base unit 12 can be shared by a number of different patients, each having their own mouthpiece unit 14. Because entirely different mouthpiece units 14 are being used by each of the patients, concerns about contamination are relatively low. One multiple patient application of the invention is in a hospital environment. For example, a nurse can carry the portable base unit 12 from bed to bed in a hospital ward to collect respiratory data from a number of different patients each having his/her own mouthpiece unit 14. The nurse then inserts the base unit 12 into a corresponding docking station 16 and the collected data is delivered to an appropriate location. Because each patient uses his/her own mouthpiece unit, the collected data is automatically indexed by patient. Accordingly, the docking station 16 can be programmed to direct the collected data to different locations based on patient identity. For example, in addition to being recorded in the hospital's records, each patient's data can be delivered to the computer of his/her personal physician.

In accordance with one embodiment of the present invention, the base unit 12 and the patient are capable of communicating with one another using ordinary speech. That is, the base unit 12 is capable of prompting/querying/instructing the patient using a synthesized voice and the patient is able to respond to the base unit 12 using his own voice. The PPM 40 uses the voice synthesis unit 46 to convert prompts and queries for the patient to synthesized electrical voice signals. These synthesized electrical voice signals are then delivered to the speaker 54 which generates audible voice signals that can be heard by the patient. When the patient hears an audible query, he can then respond to the query using his own voice. The response is picked up by the microphone 56 which converts it to an electrical voice signal and delivers it to the PPM 40. The PPM 40 then uses the voice recognition unit 48 to recognize the meaning of the words of the response. The voice recognition unit 48 can utilize any of a number of different voice recognition algorithms to perform the recognition function. After a verbal response has been recognized, the PPM 40 uses the response to determine a next course of action. If the verbal response was unrecognizable using the voice recognition unit 48, the PPM 40 repeats the query for the patient.

Using the voice synthesis unit 46 and the speaker 54, the PPM 40 can give the patient instructions during a measurement. For example, after the PPM 40 has determined that the base unit 12 is ready for a measurement, it can say "PLEASE BLOW NOW." Even during the patient's breath, the PPM 40 can coach the patient to use maximum effort by stating something like, "BLOW HARDER! BLOW, BLOW, BLOW!" After the measurement, the PPM 40 can indicate the results of the measurement to the patient by stating, for example, "THANK YOU. YOUR PEAK FLOW IS SATISFACTORY." Similarly, the PPM 40 can recommend a dosage of medication by stating, for example, "YOU MAY TAKE MDI MEDICATION NOW. THANK YOU." After the medication has been administered, the PPM 40 can ask the patient to take another test to determine the effect of the medication. All of these activities of the patient are recorded by the PPM 40 in the performance event memory 42 along with corresponding time information.

As described above, the PPM 40 is also capable of querying the patient as to symptoms that are relevant to his respiratory condition. The patient's responses are then time tagged and stored within the performance event memory 42 for later analysis by the physician. For example, the PPM 40 can ask the patient "ARE YOU EXPERIENCING ASTHMA SYMPTOMS? PLEASE ANSWER YES OR NO." The content of the patient's verbal answer is then recorded. As can be appreciated, symptom information can prove invaluable to a physician who is trying to develop an optimal treatment regimen for a patient as it can indicate such things as the patient's reaction to a medication, the duration of the effectiveness of medication doses, the patient's reaction to other stimuli such as pollutants, allergens, and stress, and times of day when symptoms are aggravated. The PPM 40 can query the patient for symptom information, for example, at predetermined times of day, before and after medication use, or after a respiratory measurement has been made. In addition, the patient can input symptom information at any time the patient feels it will be helpful to develop an optimal treatment regimen, such as when unexpected flare-ups or attacks occur.

The wireless transceiver 44 allows the base unit 12 to communicate with, among other things, peripheral medical devices. A transducer 45, such as an antenna or infra-red diode, is coupled to the wireless transmitter 44 for use in transmitting and/or receiving wireless signals to/from external entities. The wireless transceiver 44 can utilize virtually any type of wireless energy to perform the required communication. For example, the wireless transceiver can use radio frequency, infra red (IR), visible light, or ultrasonic data transmission, to name a few.

As indicated in FIG. 1, the wireless transceiver 44 enables the base unit 12 to communicate with a smart inhaler unit 26 that has similar communication capabilities. After a patient has inhaled a dose of asthma medication from the inhaler 26, the inhaler 26 transmits a signal to the base unit 12 indicating the dose of medication taken and whether the dose was properly administered. This signal is received by the wireless transceiver 44 within the base unit 12 and information contained within the signal is recorded within the performance event memory 42 with an appropriate time stamp. The wireless transceiver 44 then transmits an acknowledgment signal to the inhaler 26 indicating that the original signal was received and recorded. If the inhaler 26 does not receive the acknowledgment signal within a predetermined period after transmitting the original signal, the inhaler 26 retransmits the signal. Alternatively, the inhaler 26 can first prompt the patient to place the inhaler 26 in a better position to communicate with the base unit 12 before retransmitting the signal. Other types of peripheral medical device (such as, for example, dry powder inhalers and pill dispenser monitors) can also be utilized in this fashion in accordance with the present invention.

In a preferred embodiment of the invention, the wireless transceiver 44 is also used for communicating with the docking station 16 when the base unit 12 is inserted within the cradle 22 thereof. That is, the docking station 16 includes means for sensing wireless signals transmitted by the base unit 12 and means for radiating wireless signals that can be sensed by the base unit 12. For example, if radio frequency signals are used to provide the wireless communication functionality, the docking station 16 will have a radio frequency transceiver and an antenna for supporting the wireless communication. Wireless communication between the base unit 12 and the docking station 16 is desirable because it does not require the completion of an electrical circuit (i.e., contact between conductors) for communication to be enabled. However, it should be appreciated that wired communication connections between the base unit 12 and the docking station 16 can alternatively be used in accordance with the present invention. For example, spring loaded communication terminals within the cradle 22 can be provided for contacting stationary terminals on the outside of the base unit 12 when the base unit 12 is inserted into the cradle 22 to provide a communication path between the units.

Figure 3:
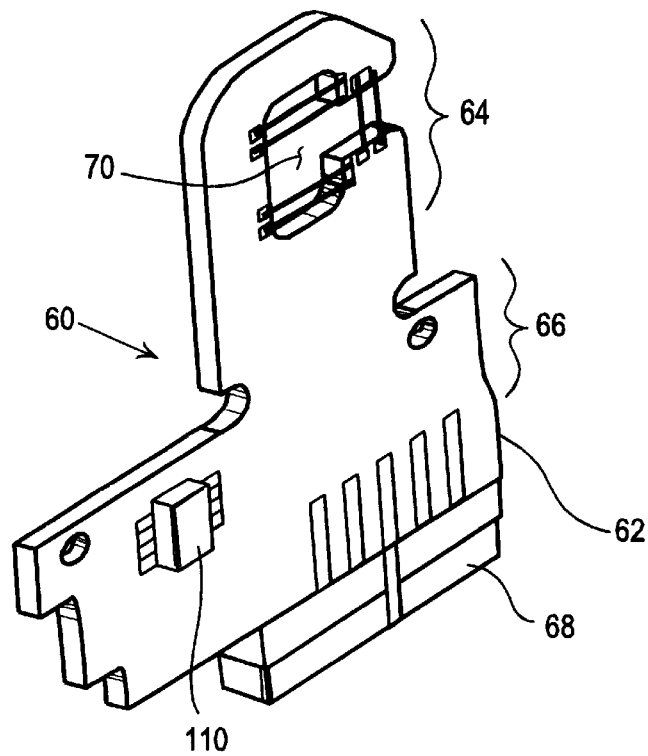
FIGS. 3 and 4 are a perspective view and a top view, respectively, of a flow board in accordance with one embodiment of the present invention.
Figure 4:
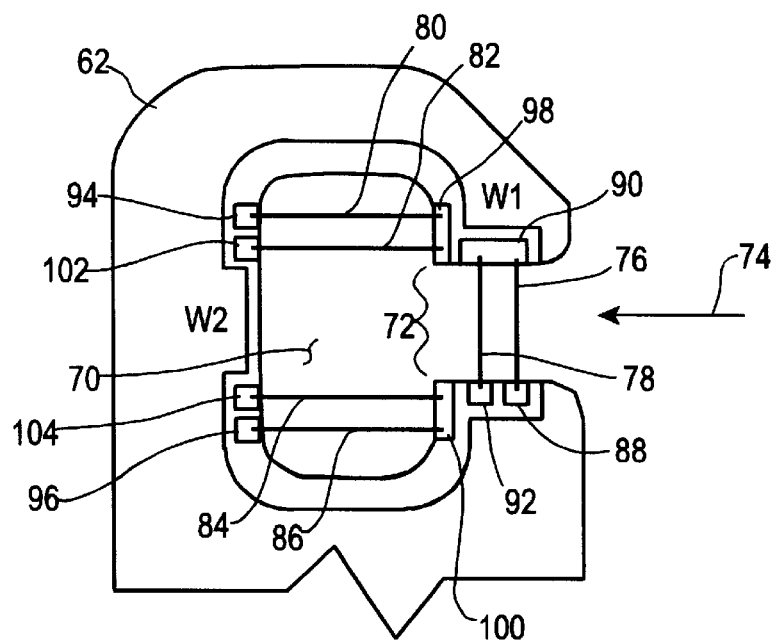

In a preferred embodiment of the present invention, the mouthpiece unit 14 is a disposable unit that, as described above, is dedicated for use by a single patient during its useful lifetime. Therefore, the mouthpiece unit 14 preferably uses relatively inexpensive parts and is relatively simple to manufacture. FIGS. 3 and 4 are an isometric view and a top view, respectively, of a flow board assembly 60 that can be used in the mouthpiece unit 14 in accordance with the present invention. The flow board assembly 60 includes the sensors required to derive raw data from a patient's breath, a connector for use in connecting the mouthpiece unit 14 to the base unit 12, and all electronics that will be located within the mouthpiece unit 14 for use during testing. During manufacture of the mouthpiece unit 14, the portion of the flow board assembly 60 having the sensors is housed in a cylindrical air flow chamber 32 (see FIG. 1) having an orifice 30. The air flow chamber 32 is operative for directing the patient's breath over the sensors so that accurate readings can be made. The air flow chamber 32 will also have one or more vent ports (not shown) for allowing the patient's breath to escape from the chamber 32 during testing. Both the flow board assembly 60 and the cylindrical air flow chamber 32 can be manufactured relatively inexpensively and integration of the two parts can be as simple as snapping together two sides of the air flow chamber 32 around the relevant portion of the flow board assembly 60.

As shown in FIGS. 3 and 4, a hot wire sensor arrangement is used in the illustrated embodiment. A description of hot wire sensor arrangements can be found in U.S. Pat. No. 5,518,002, entitled "Portable Electronic Spirometric Device", which is commonly owned by the assignee of the present invention and which is hereby incorporated by reference. As illustrated, the flow board assembly 60 includes (a) a shaped circuit board 62 having a sensor portion 64 and an electronics portion 66 and (b) a connector 68. The sensor portion 64, in this embodiment, includes a plurality of hot wire sensors disposed about an aperture 70 in the circuit board 62 for use in sensing parameters of the patient's breath. As described above, the sensor portion 64 of the circuit board 62 is housed within the air flow chamber 32 during operation. The electronics portion 66 of the circuit board 62 includes all of the electronics of the mouthpiece unit 14 and is preferably located outside of the air flow chamber 32 during operation. The electronics within the electronics portion 66 and the sensor or sensors within the sensor portion 64 of the circuit board 62 are each linked to one or more pins in the connector 68 via appropriate conductors such as fingers that can be inserted into the connector 68.

FIG. 4 is a top view of the sensor portion 64 of circuit board 62. As shown, the aperture 70 in the circuit board 62 is extended out through a side of the circuit board 62 by a throat 72. The throat 72 is in a position to first receive air flow 74 from a patient's breath when the flow board 60 is mounted within the air flow chamber 32. The flow sensor of this embodiment includes a number of hot wires. In particular it includes a first hot wire 76 and a second hot wire 78 that extend across an upper edge of the throat 72. In this embodiment also, a number of hot wires constitute a temperature sensor. This temperature sensor includes a third hot wire 80, a fourth hot wire 82, a fifth hot wire 84, and a sixth hot wire 86 extends across the aperture 70 in a direction perpendicular to the direction of the first and second hot wires 76, 78. The first and second hot wires 76, 78 are connected in series with one another. That is, the first hot wire 76 is connected at one end to a first input pad 88 and at the other end to a center tap pad. 90 and the second hot wire 78 is connected at one end to the center tap pad 90 and at the other end to a first output pad 92. Similarly, the third, fourth, fifth, and sixth hot wires 80–86 are connected in series using a second input pad 94, a second output pad 96, two center tap pads 98, 100, and two support pads 102, 104. The two support pads 102, 104 are electrically connected to one another by other means to complete the series connection of temperature sensor hot wires. The first input and output pads 88, 92 and the center tap pad 90 of the flow sensor and the second input and output pads 94, 96 of the temperature sensor are each connected to individual pins within the connector 68 for access by the measurement unit 38 of the base unit 12 during a reading.

The unique sensor arrangement of this one possible embodiment described above allows the direction of air flow in the air flow chamber 32 to be detected. Importantly, this allows patient errors, such as blowing into the wrong end of the air flow chamber 32 (i.e., into the vent holes) or inhaling instead of exhaling, to be detected and corrected. With reference to FIG. 4, proper air flow direction is indicated by the arrow 74 indicating that properly blown air will encounter first hot wire 76 before it reaches second hot wire 78. Accordingly, the first hot wire 76 will experience more of a cooling effect than the second hot wire 78. This situation creates an imbalance that can be detected and measured by monitoring the signal values on the input, output, and center tap pads 88, 92, 90. If the imbalance is in the wrong direction, then it is assumed that patient has committed an error and an appropriate message is displayed (or spoken) to the patient.

In one approach, the air flow reading is taken across the series combination of the first and second hot wires 76, 78 and thus only requires monitoring of the first input and output pads 88, 90. Similarly, an air temperature reading can be taken across the series combination of the third, fourth, fifth, and sixth hot wires 80–86 and thus only requires monitoring the second input and output pads 94, 96. Use of the open throat 72 configuration reduces air turbulence around the sensors that can adversely affect the accuracy of the measurements.

In a preferred embodiment, nickel wire having a suitable diameter is used for the hot wires 76–86, although any similar type of wire can be used (such as, e.g., platinum or gold based wire). The pads 88–104 are preferably gold plated and each wire is connected to the corresponding pads using wire bond welding (although other connection techniques, such as soldering, can also be used).

Referring back to FIG. 3, the electronics portion 66 of the circuit board 62 includes a memory 110 for use in storing information about the corresponding mouthpiece unit 14. The memory 110 is preferably a non-volatile semiconductor memory (e.g., an EEPROM) that will not lose its contents during periods when little or no power is being supplied to the memory 110 (such as when the mouthpiece unit 14 is detached from the base unit 12). In a preferred embodiment, the memory 110 is used to store patient identification information identifying a patient having exclusive use of the corresponding mouthpiece unit 14. The patient identification information will normally be stored in the memory 110 by the physician when he assigns the corresponding mouthpiece unit 14 to a patient for the patient's exclusive use. This identification information is preferably never changed during the useful life of the mouthpiece unit 14. The patient identification information can include, for example, the patient's name and/or a unique patient identifier string assigned to the patient (e.g., the patient's social security number). In one embodiment, it is possible to also store calibration and operating information related to the particular sensors within the sensor portion 64 of the corresponding circuit board 62. The calibration data can be stored in the memory 110 during manufacture and could be changed periodically as a result of recalibrations.

The memory 110 is operatively connected to pins within the connector 68 to provide access to the stored information by the base unit 12 during operation. In one embodiment of the invention, the PPM 40 knows where particular information is stored within the memory 110 and retrieves this information when the mouthpiece unit 14 is initially inserted into the base unit 12. The information is then stored within the base unit 12 at least until the mouthpiece unit 14 is removed. The PPM 40, as discussed previously, uses the patient identification information retrieved from the memory 110 to index the patient performance information stored in the performance event memory 42. In situations where multiple patients are sharing a single base unit 12, this indexed storage allows the information of individual patients to be accessed from the base unit 12 by the docking station 16. In multiple patient situations, the PPM 40 can include multiple stored treatment plans, each corresponding to a different patient. In such cases, the PPM 40 can use the patient identification information from the mouthpiece unit 14 to determine which physician treatment plan to follow for a patient currently using the base unit 12.

The sensor calibration information stored within the memory 110 will be retrieved by the measurement unit 38 when the mouthpiece unit 14 is inserted into the base unit 12. Alternatively, the calibration information can be retrieved by the PPM 40 which transfers it to the measurement unit 38. The measurement unit 38 then uses the calibration information to transform the raw data received from the sensors into meaningful measurement data.

In one embodiment of the invention, the memory 110 also stores respiratory performance information related to the corresponding patient. For example, the patient's personal best PEFR score can be stored in the memory 110 for later comparison. The PPM 40 can read this score from the memory 110 and compare it to a current PEFR reading for the patient. If the current score is higher than the personal best, the patient is congratulated and the previous personal best score within the memory 110 is replaced by the current score. If the current score is lower, the patient is informed of how much lower it is. The memory 110 can also include information identifying the patient's physician (e.g., physician's name and telephone number). This information can be used by the docking station 16, for example, to transfer a particular patient's respiratory-related information to the appropriate physician data collection station 18 (see FIG. 1).

Figure 5:
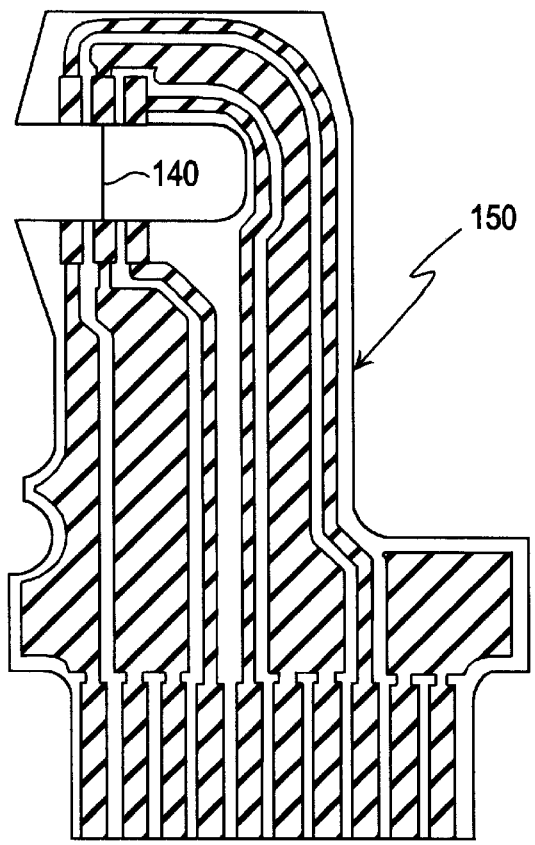
FIG. 5 is a plan view of a circuit board in accordance with another embodiment of the present invention that has a single hot wire.
Figure 6:
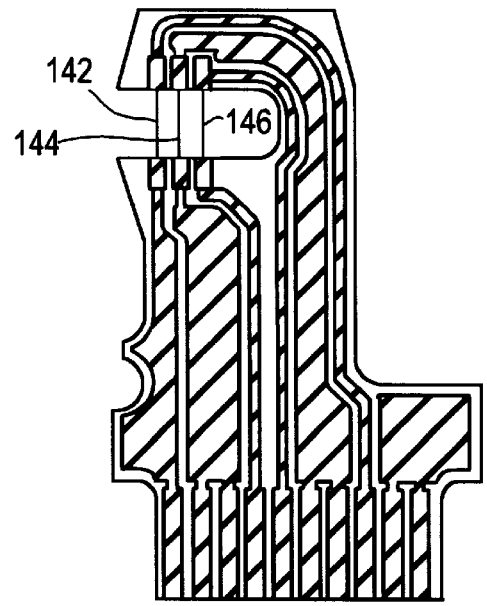
FIG. 6 is a plan view of a circuit board in accordance with still another embodiment of the present invention that also has a single hot wire.

With reference to FIGS. 5 and 6, other embodiments of a hot wire sensor configuration are illustrated. The embodiment of FIG. 5 has a single hot wire 140, connected to its circuit board 150. The hot wire 140 is utilized to monitor the patient's exhalation, or possibly inhalation. A heated wire, placed in a moving fluid (air) will dissipate heat in proportion to the velocity of the fluid moving past it. Using this principle, the volume and flow rate of air passing through a fixed orifice can be calculated. This embodiment is less complex in construction and operation, in comparison with the multiple hot wire embodiments. FIG. 6 illustrates a multi-wire embodiment. When a multi-wire configuration is used, the direction of air flow can be detected. The heated wire is positioned as the center wire 144 of a three wire group, with sensing circuitry attached to all three wires 142, 144, & 146. During air flow, the upstream wire (142 or 146) will experience a relatively small change in temperature, possibly even cooling. The heated wire 144 will be used to detect the volume and rate of the flow. Due to the heat dissipated by the heated wire, the downstream wire (the other of 142, 146) will experience a larger temperature change than the upstream wire. Using this differential, direction of flow can be determined. When inhaling, the downstream wire (one of 142 or 146) is the wire that is farthest away from the patient's mouth. When exhaling, the downstream wire (the other of 142 or 146) is the wire closest to the patient's mouth.

Figure 7:
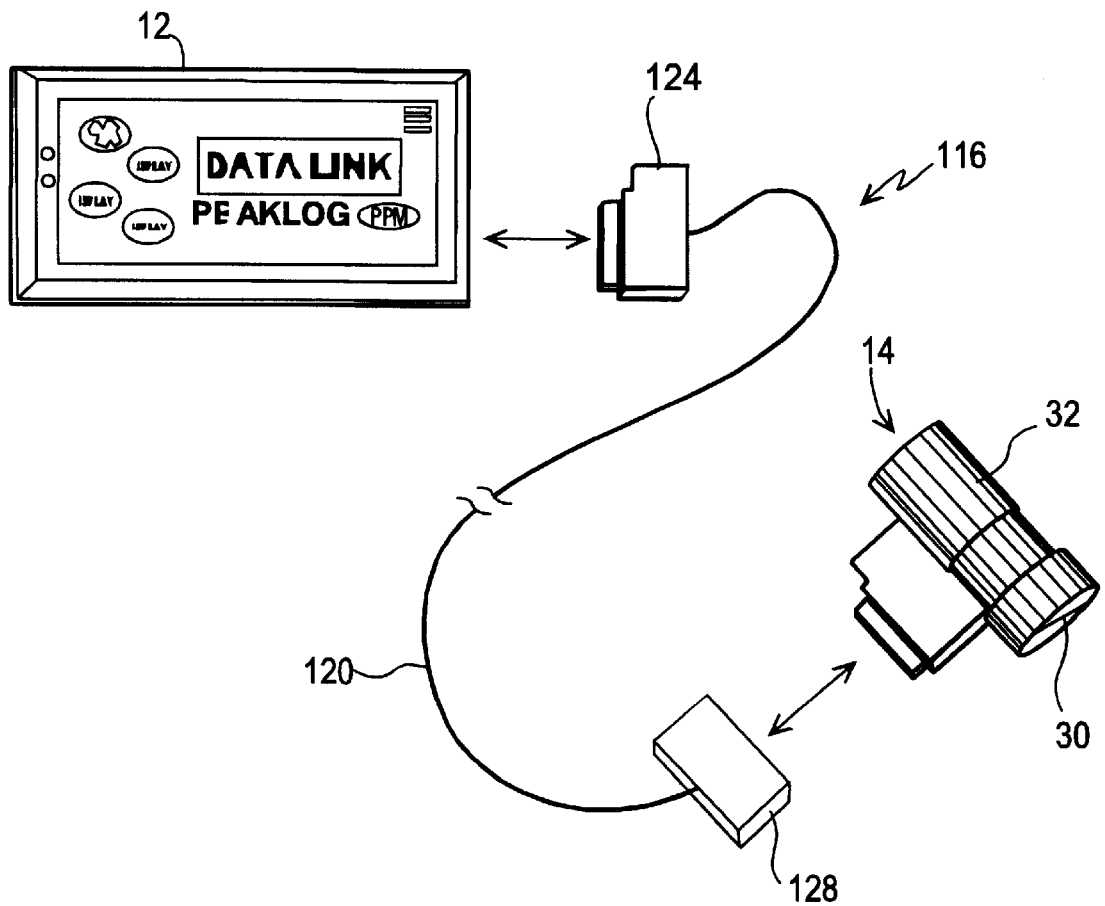
FIG. 7 is a diagram illustrating the use of a cable to connect a mouthpiece unit and a base unit in accordance with the present invention.

FIG. 7 illustrates the use of a cable assembly 116 to connect the mouthpiece unit 14 to the base unit 12. The cable assembly 116 allows a patient to perform a respiratory test from a position that is somewhat removed from the base unit 12. This additional distance between the patient and the base unit 12 can help to reduce any hygiene concerns that a patient may have with regard to the shared base unit 12. In addition, the additional distance afforded by the cable assembly 116 allows the patient to view the front panel of the base unit 12 during the testing. The cable assembly 116 preferably has a first or proximal connector 124 on one end that is identical to the connector on the base unit 12 and a second or distal connector 128 on the other end that is identical to the connector 68 on the mouthpiece 14 so that the cable assembly 116 can be directly inserted between the units without adapters. A cable member 120 is intermediate and connected to each of the first and second connectors 124, 128. In a preferred embodiment, the cable member 120 is at least 18 inches long.

Figure 8:
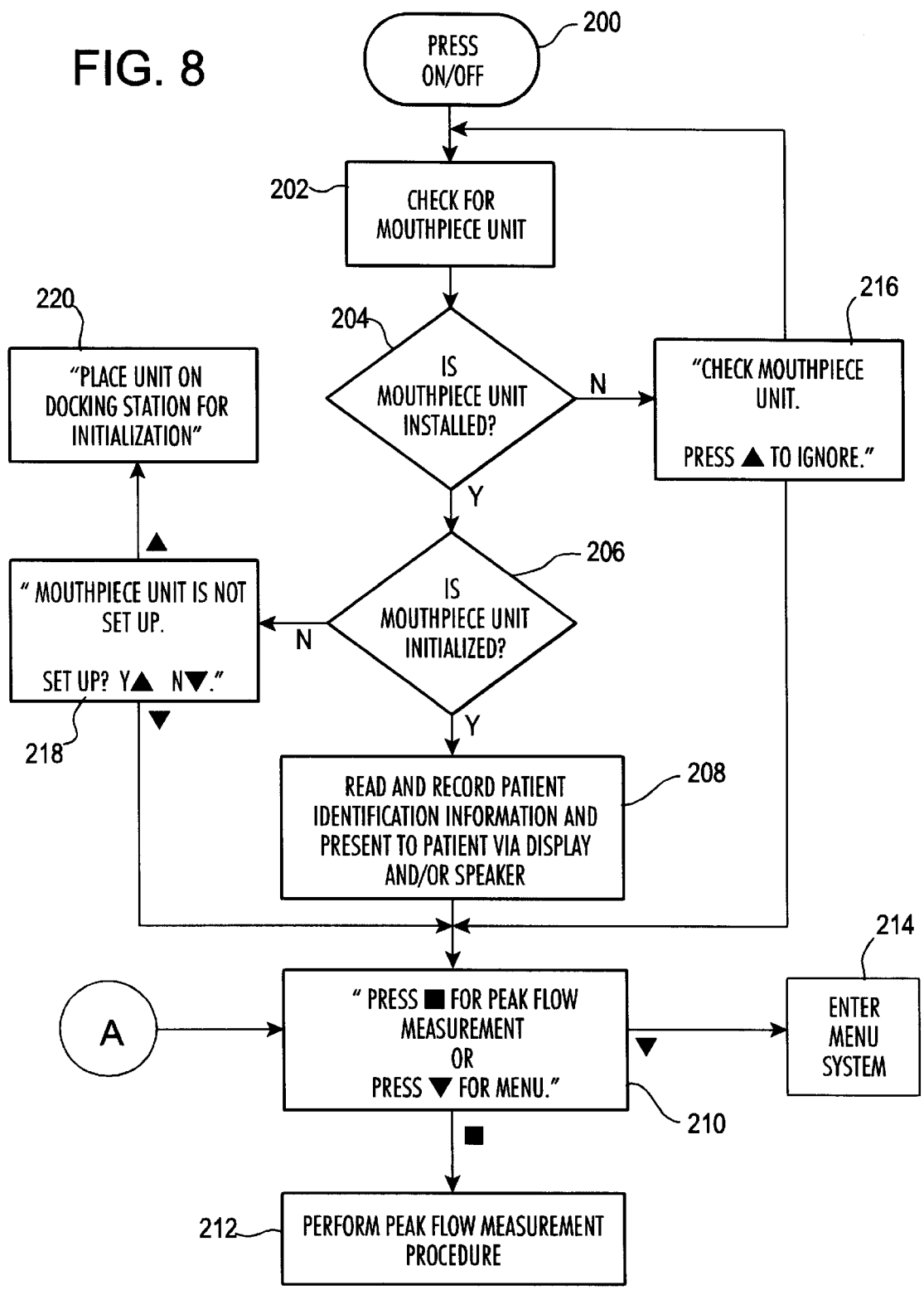
FIGS. 8, 9 and 10 are flowcharts illustrating an operating procedure followed by a base unit in one embodiment of the present invention.
Figure 9:
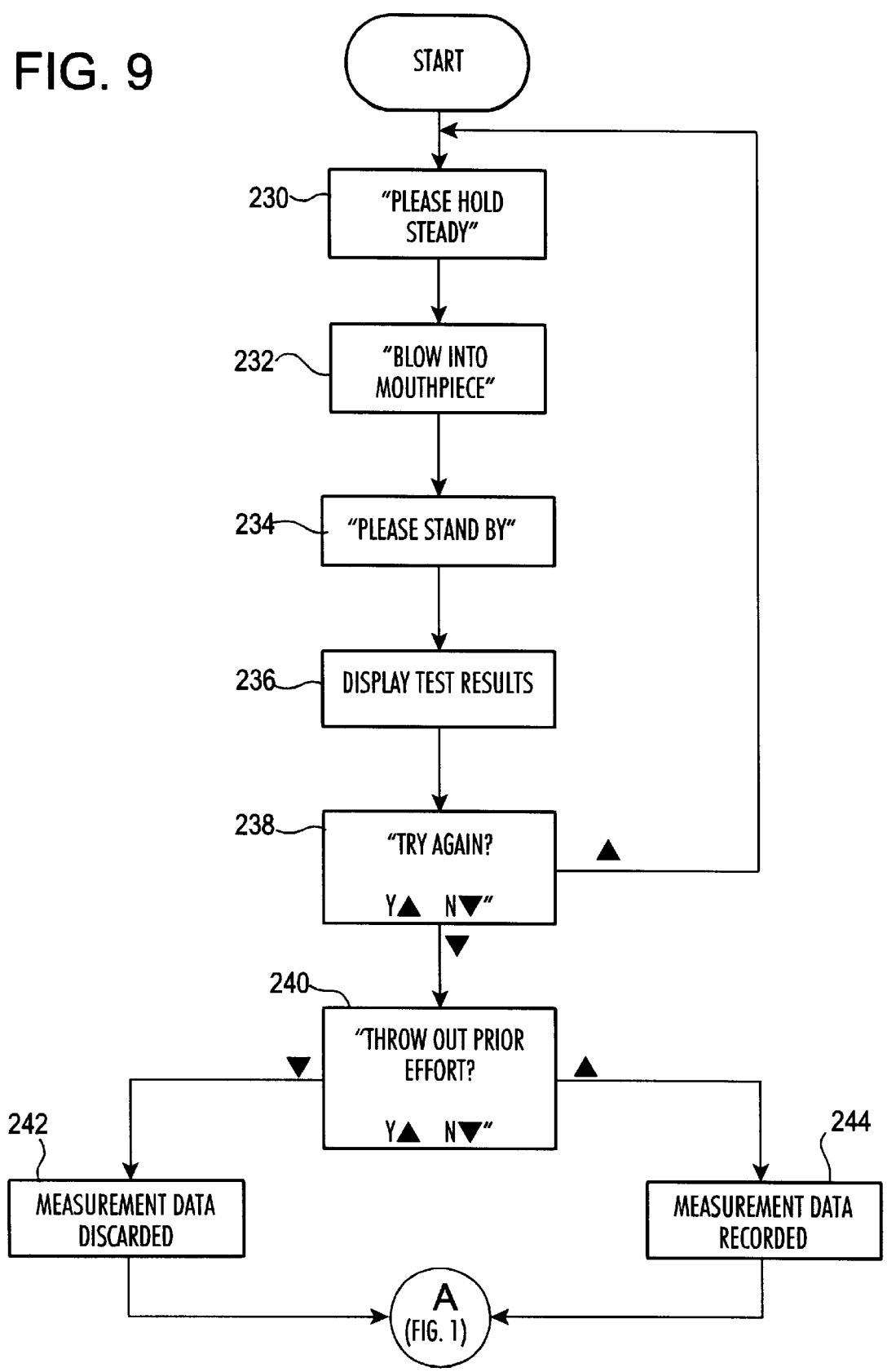
Figure 10A:
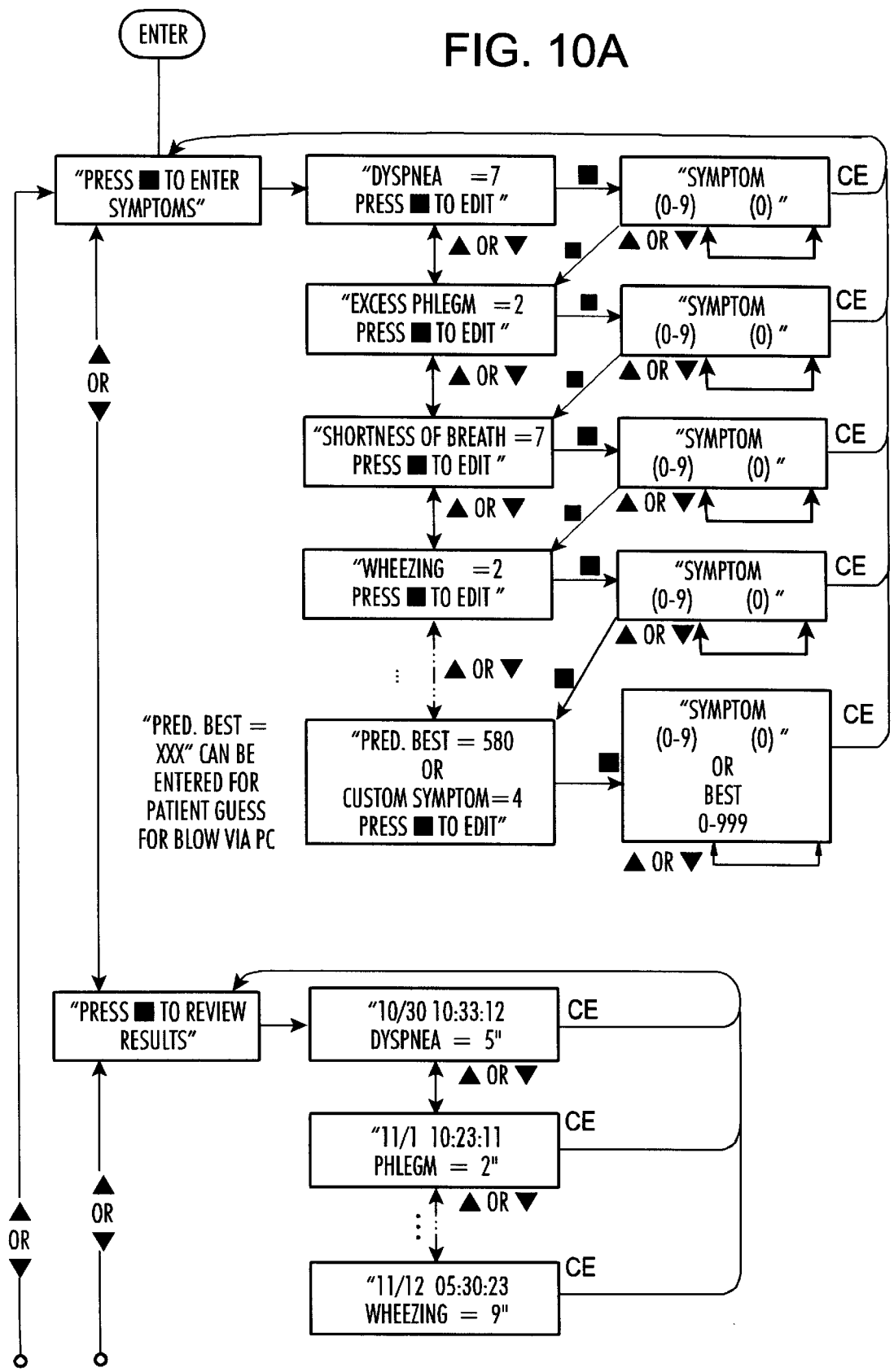
Figure 10B:
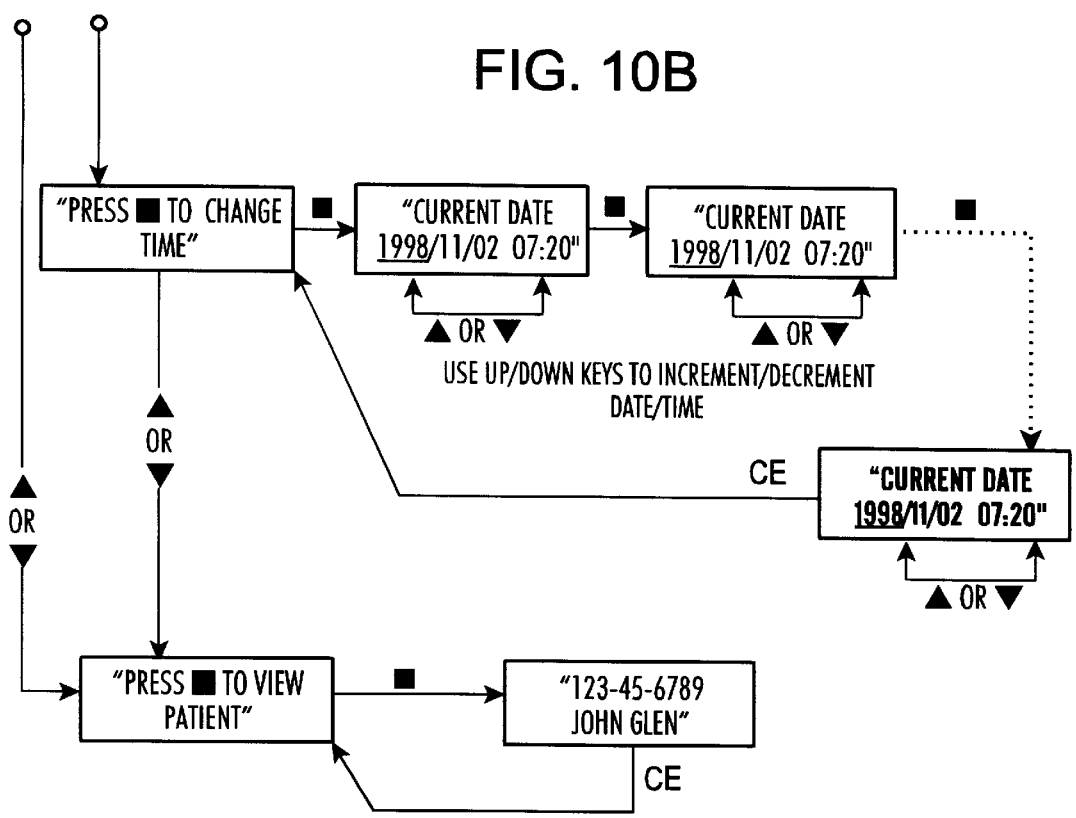

FIGS. 8, 9 and 10 are flowcharts illustrating an operating procedure followed by base unit 12 in one embodiment of the present invention. The operating procedure begins when a patient activates the base unit 12 by pressing an on/off key on the front panel of the base unit 12 (step 200). The base unit 12 immediately checks to determine whether a mouthpiece unit 14 is attached to the base unit 12 (steps 202, 204). If a mouthpiece unit 14 is installed, the base unit 12 then determines whether the mouthpiece unit 14 has been initialized with, for example, patient identification information (steps 206). If the mouthpiece unit 14 has been initialized, the base unit 12 reads and records the patient identification information stored in the mouthpiece unit 14 (step 208). In addition, the base unit 12 displays the patient identification information to the patient on the LCD display 50 and may also verbally indicate the patient identification information using synthesized speech (step 208). After the patient information has been displayed for a predetermined amount of time, the base unit 12 displays the following choice "PRESS ■ FOR PEAK FLOW MEASUREMENT OR ▼ FOR MENU" (step 210). If the patient wishes to take a reading, he presses the ■ key on the front panel of the base unit 12 and a peak flow measurement procedure is initiated (step 212). One such peak flow measurement procedure is illustrated in the flowchart of FIG. 7. If the patient wishes to use any of the other functions of the base unit 12, he presses the ▼ key and enters a menu system (step 214).

In step 204 above, if the base unit 12 determines that a mouthpiece unit 14 is not installed, it will prompt the patient with a statement such as "CHECK MOUTHPIECE UNIT. PRESS ▲ TO IGNORE." (step 216). Some of the functions of the base unit 12 do not require a mouthpiece 14 to be inserted. In such cases, the patient simply presses the ▲ key on the front panel of the base unit 12 and he proceeds to selection step 210 described above. If the ▲ key is not pressed, the base unit 12 will continually check for a mouthpiece unit 14 (i.e., repeatedly return to step 202) until one is detected. In step 206 above, if the base unit 12 detects that the mouthpiece unit 14 has not been initialized, the patient is given the option to initialize the unit 14. That is, the base unit 12 displays "MOUTHPIECE IS NOT SETUP. SETUP? Y▲ N▼" (step 218). If the patient decides that he wants to initialize the mouthpiece unit 14 with his identification information, he presses the ▲ key and the base unit 12 displays "PLACE UNIT ON DOCKING STATION FOR INITIALIZATION" (step 220). The patient then inserts the base unit 12 with mouthpiece unit 14 into the docking station 16 and presses appropriate keys on the front panel of the docking station 16 to start the initialization process. If the patient does not wish to initialize the mouthpiece unit 14 at this time, he presses the ▼ key and proceeds to selection step 210 described above.

FIG. 9 is a flowchart illustrating a procedure for performing a peak flow measurement in accordance with one embodiment of the present invention. When the patient indicates that he wishes to perform a peak flow measurement, the base unit 12 displays the statement "PLEASE HOLD STEADY" (step 230). This gets the patient ready for the measurement and also allows the base unit 12 to perform the calibrations needed to get accurate results from the measurement. After a short period of time, the base unit 12 displays "BLOW INTO MOUTHPECE" (step 232) after which the patient blows as hard as he can into the orifice 30 in the mouthpiece unit 14. The base unit 12 then displays "PLEASE STANDBY" as it processes the raw measurement data from the mouthpiece unit 14 (step 234). The base unit 12 then displays the test results to the patient (step 236). The test results can be displayed in multiple stages if desired. For example, standard numerical test figures can first be displayed such as, for example, PEFR and FEV1 levels. In one embodiment, a display of the respiratory maneuver can be provided. After these are displayed for a predetermined period of time, other indications, such as percentage of personal best and zone, can be displayed to indicate to the patient how his present reading compares to past performance. However, to be able to determine these indications, the base unit 12 must have access to personal best information for the present patient, such as from the mouthpiece unit 14.

After the test results have been displayed, the base unit 12 will ask the patient if he wants to perform the test again. That is, the base unit 12 will display the question "TRY AGAIN? Y▲ N▼" (step 238). If the patient wishes to perform the test again, he presses the ▲ key and the test procedure is repeated. If the patient does not wish to repeat the procedure, he presses the ▼ key. The base unit 12 then displays the question "THROW OUT PREVIOUS EFFORT? Y▲ N▼" (step 240). If the patient does not want the reading recorded, he presses the ▲ key and the measurement data is discarded (step 242). Otherwise, the patient presses the ▼ key and the data is recorded along with the relevant date/time and patient identification data (step 244). In either case, control is then passed back to selection step 210 in the process of FIG. 6.

FIG. 10 is a flowchart illustrating a menu system that is used by the base unit 12 in one embodiment of the present invention. After the patient indicates that he wishes to enter the menu system, a first menu choice is presented on the display of the base unit 12. For example, as illustrated in FIG. 8, the base unit 12 displays "PRESS ■ TO ENTER SYMPTOMS" (step 250). The patient is now able to scroll through the other menu choices using the ▲ key and the ▼ key. In the illustrated embodiment, the other menu choices are "PRESS ■ TO REVIEW RESULTS", "PRESS ■ TO CHANGE TIME", and "PRESS ■ TO VIEW PATIENT". When the patient finds the menu choice he is interested in, he presses the ■ key and he will then be able to perform the associated function. For example, if the patient wishes to record symptoms, he presses the ■ key while "PRESS ■ TO ENTER SYMPTOMS" is being displayed and he is then within a submenu of possible symptoms. The patient is able to scroll through the symptoms using the ▲ key and the ▼ key. When an appropriate symptom is being displayed, the patient presses the ■ key and he is then able to scroll through a number of symptom values (e.g., 0–9) that describe the severity of the present symptom. When the base unit 12 displays a value that accurately describes the patient's current symptom, the patient presses the ■ key and the symptom value is recorded along with the present time/date. Control is then returned to the symptom submenu where the patient can record another symptom. Alternatively, the patient can press the CE key after the symptom value has been displayed and the symptom value is recorded in the same manner, but control returns to the main menu. Similar procedures are followed for the other menu items. At any time, the patient whose mouthpiece unit 14 is presently installed in the base unit 12 can be determined by pressing the ■ key in response to the "PRESS ■ TO VIEW PATIENT" menu item.

It should be noted that each of the displayed messages described above can also be "spoken" to the patient using the voice synthesis functionality. Similarly, the voice recognition functionality can be used to recognize spoken responses from the patient. For example, responses such as "up", "down", and "select" can be recognized by the base unit 12 to carry out the above procedures.

Figure 11:
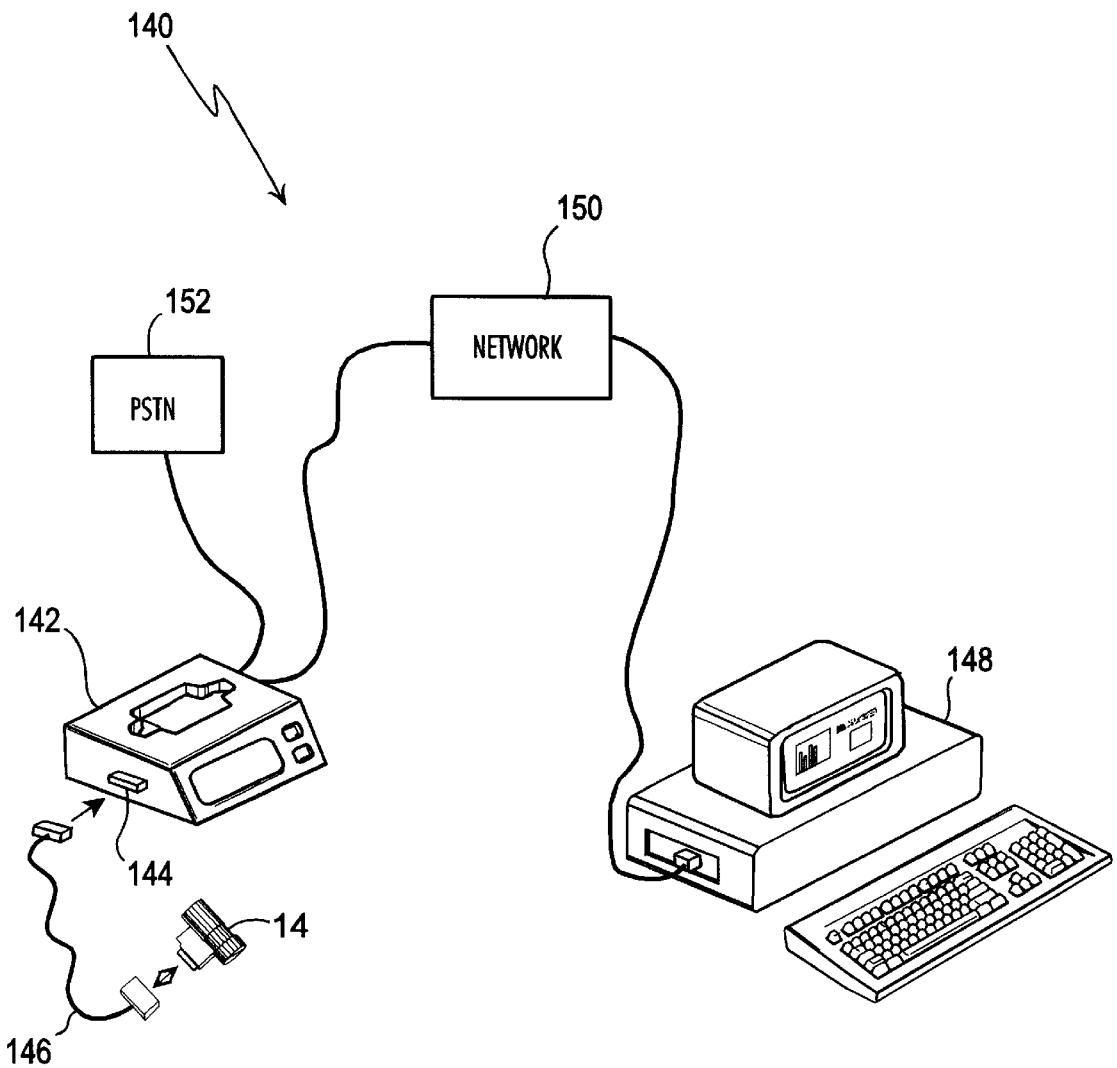
FIG. 11 is a diagram illustrating a system in accordance with another embodiment of the present invention.

FIG. 11 is a diagram illustrating a system 140 in accordance with another embodiment of the present invention. The system 140 is for use in situations where the mobility of the base unit is less important. The system 140 is similar in operation to the system 10 illustrated in FIG. 1, except that functions of the base unit 12 and the docking station 16 of FIG. 1 have been combined into a single stationary base unit 142. The stationary base unit 142 will typically be located in a hospital or other medical establishment where a number of patients, each having their own mouthpiece unit 14, may be located. Because a single unit is used to perform both the data collection and the communications functions, problems such as forgetting to place a portable base unit in the cradle at the end of the day or battery depletion during a test, are avoided. The stationary base unit 142 includes an input port 144 for insertion of a patient's mouthpiece unit 14, either directly or through a cable 146. As before, the base unit 142 will retrieve patient identification information from the mouthpiece unit 14 and store all subsequent test results corresponding to that patient within a memory inside the base unit 142, along with date and time information.

In a hospital environment, one or more base units 142 will generally be kept at convenient locations within the hospital for use by patients. When it is time for a particular patient to take a reading, the patient is brought to a base unit 142 along with his personalized mouthpiece unit 14. The patient inserts his mouthpiece unit 14 into the base unit 142 and is then instructed by the base unit 142 (via an LCD readout or synthesized speech) how to proceed with the measurement. After the measurement has been taken, the resulting data is recorded as described previously and the base unit 142 tells the patient the results of the test. The data is subsequently transferred to an attending physician's computer 148 via, for example, hospital network 150 for use in treating/monitoring the patient while he is in the hospital. The data can also be stored in the hospital's computer files on network 150 to maintain appropriate records for the patient. The stationary base unit 142 can also be connected to a PSTN 152 or other public communication network for communicating with entities outside the hospital.

For immobile patients, the base unit 142 can be detached from the network 150 and brought to the patient's bedside. Although the stationary base station 142 will normally run on AC power from a wall socket, battery backup power can be provided for energizing the base station 42 during such procedures. Alternatively, the base unit 142 can be plugged into a wall socket in the immobile patient's room. The base unit 142 is later reattached to the network 150 and the appropriate data transfers are carried out.

Significantly, a patient who utilizes a portable base unit 12 (as illustrated in FIG. 1) with a personalized mouthpiece unit 14 during his normal daily routine at home can bring his personalized mouthpiece unit 14 with him during stays in the hospital for use with a stationary base unit 142 (as illustrated in FIG. 8) at the hospital. Thus, the stationary base unit 142 at the hospital will be able to use the patient identification information (and other information) already stored in the mouthpiece unit 14 to automatically and chronologically record all respiratory measurement results for the patient while he is in the hospital. In addition, the stationary base unit 142 at the hospital will be able to update stored personal best information, and other stored information, within the mouthpiece unit 14 as needed to keep the patient's mouthpiece unit 14 current. Because patients will be using their own personal mouthpiece units 14, the hospital need not provide and program new mouthpieces for every new respiratory patient admitted to the hospital, resulting in significant cost savings for the hospital and the patient.

Storage of physician identification information within the memory 110 of the mouthpiece unit 14, as discussed previously, is especially advantageous in a hospital scenario. For example, the hospital's base unit 142 can use physician identification information stored within a patient's mouthpiece unit 14 to transfer all respiratory-related data collected from the patient while in the hospital directly to the computer of the patient's personal physician (via, for example, the PSTN 152 or other public communications network) for the physician's use and analysis. As described above, the information will also normally be delivered to the attending physician in the hospital and be stored in the hospital's records.

As can be appreciated, some of the functions of the portable base unit 12 will not be available from the stationary base unit 142, such as patient prompts when it is time to take a measurement. However, while a patient is in the hospital, these functions are generally performed by nurses and/or other hospital personnel.

Although the present invention has been described in conjunction with its preferred embodiments, it is to be understood that modifications and variations may be resorted to without departing from the spirit and scope of the invention as those skilled in the art readily understand. Such modifications and variations are considered to be within the purview and scope of the invention and the appended claims.

What is claimed is:

1. A method for obtaining information related to respiratory functions from a number of patients, comprising:

providing a base unit;

providing a first mouthpiece assembly;

providing a second mouthpiece assembly;

coupling said first mouthpiece assembly to said base unit;

obtaining first patient information for a first patient including receiving patient identification information by said base unit from said first mouthpiece assembly when said first patient identification information is present in said first mouthpiece assembly;

uncoupling said first mouthpiece assembly from said base unit;

coupling said second mouthpiece assembly to said base unit; and obtaining second patient information for a second patient including receiving patient identification information by said base unit from said second mouthpiece assembly when said second patient identification information is present in said second mouthpiece assembly.

2. The method, as claimed in claim 1, wherein:

said step of providing a base unit includes providing a base unit having a measurement module for processing raw measurement data received from a mouthpiece assembly coupled to said base unit.

3. A method, as claimed in claim 2, wherein:

said step of providing a base unit includes providing a base unit having a storage unit for storing measurement results generated by said measurement module.

4. A method, as claimed in claim 1, wherein:

said base unit includes a processor and said first patient information includes first patient data related to at least one respiratory function of said first patient and said step of obtaining said first patient information includes correlating said first patient data with said first patient identification information.

5. A method, as claimed in claim 4, wherein:

said base unit includes a base unit memory and said first mouthpiece assembly includes a first mouthpiece memory and said step of obtaining said first patient information includes storing said first patient data correlated with said first patient identification information in said base unit memory.

6. A method, as claimed in claim 5, wherein:

said step of obtaining said second patient information includes storing second patient data correlated with said second patient identification information in memory locations of said base unit memory previously having said first patient data correlated with said first patient identification information.

7. A method, as claimed in claim 1, wherein:

said step of obtaining said first patient information includes checking whether said first mouthpiece assembly has said first patient identification information.

8. A method, as claimed in claim 7, wherein:

said step of obtaining said first patient information includes establishing communication between a docking station and said first mouthpiece assembly when said first mouthpiece assembly does not have said first patient identification information and then downloading said first patient identification information to a first mouthpiece memory of said first mouthpiece assembly using said docking station.

9. A method, as claimed in claim 1, wherein:

said step of obtaining said first patient information includes exhaling by the first patient into said first mouthpiece assembly and deciding by the first patient whether to store first patient data related to said exhaling step.

10. A method, as claimed in claim 1, wherein:

said step of obtaining said first patient information includes entering, by the first patient, information related to a first patient symptom into a base unit memory of said base unit.

11. A method, as claimed in claim 10, wherein:

said entering step includes entering a magnitude by the first patient of said information related to the first patient symptom, with said magnitude being indicative of a degree of the first patient symptom.

12. A method, as claimed in claim 1, wherein:

said first mouthpiece assembly comprises a cable assembly including a proximal end and a distal end and having a length, wherein said step of coupling said first mouthpiece assembly includes connecting said proximal end of said cable assembly to said base unit, wherein said length of said cable assembly allows a patient blowing into a sensor unit of said first mouthpiece assembly to simultaneously view a display on said base unit.

13. A method, as claimed in claim 1, wherein:

said step of coupling said first mouthpiece assembly includes installing a cable assembly between said first mouthpiece assembly and said base unit.

14. A system for obtaining information from a number of patients related to respiratory functions, comprising:

a base unit including a processor and a base unit memory for storing patient information, said base unit being located at one of: (i) a home of at least a first patient and (ii) a hospital;

a first mouthpiece assembly that can be connected to said base unit and including a first mouthpiece memory that stores first patient identification information; and a second mouthpiece assembly that can be connected to said base unit and including a second mouthpiece memory that stores second patient identification information;

wherein said processor is used to obtain said first patient identification information from said first mouthpiece memory when said first mouthpiece assembly is connected to said base unit at said one of the home and the hospital and said processor is used to obtain said second patient identification information from said second mouthpiece memory when said second mouthpiece assembly is connected to said base unit at said one of the home and the hospital.

15. A system, as claimed in claim 14, wherein:

said base unit includes a display for displaying information related to patient symptoms including at least one of the following: dyspnea, phlegm, shortness of breath, and wheezing.

16. A system, as claimed in claim 14, wherein:

said base unit includes input means for inputting at least one magnitude related to a first symptom and in which said one magnitude relates to a degree of the first symptom as determined by a patient using said base unit.

17. A system for obtaining information from a number of patients related to respiratory functions, comprising:
- a base unit including a processor and a base unit memory for storing patient information;
- a first mouthpiece assembly that can be connected to said base unit and including a first mouthpiece memory that stores first patient identification information; and
- a second mouthpiece assembly that can be connected to said base unit and including a second mouthpiece memory that stores second patient identification information, and in which said base unit includes a controller that stores patient data related to patient exhalation into one of said first and second mouthpiece assemblies;
- wherein said processor is used to obtain said first patient identification information from said first mouthpiece memory when said first mouthpiece assembly is connected to said base unit and said processor is used to obtain said second patient identification information from said second mouthpiece memory when said second mouthpiece assembly is connected to said base unit.

18. A system for obtaining information from a number of patients related to respiratory functions, comprising:
- a base unit including a processor and a base unit memory for storing patient information;
- a first mouthpiece assembly that can be connected to said base unit and including a first mouthpiece memory that stores first patient identification information; and
- a second mouthpiece assembly that can be connected to said base unit and including a second mouthpiece memory that stores second patient identification information;
- a docking station that communicates with at least said first mouthpiece assembly and in which said docking station is used to download said first patient identification information to said first mouthpiece memory; and
- wherein said processor is used to obtain said first patient identification information from said first mouthpiece memory when said first mouthpiece assembly is connected to said base unit and said processor is used to obtain said second patient identification information from said second mouthpiece memory when said second mouthpiece assembly is connected to said base unit.

19. A system for obtaining information from a number of patients related to respiratory functions, comprising:
- a base unit including a processor and a base unit memory for storing patient information;
- a first mouthpiece assembly that can be connected to said base unit and including a first mouthpiece memory that stores first patient identification information;
- a second mouthpiece assembly that can be connected to said base unit and including a second mouthpiece memory that stores second patient identification information; and
- a cable assembly for use in connecting said first mouthpiece assembly to said base unit, said cable assembly having a first connector that is compatible with a connector on said base unit and a second connector that is compatible with a connector on said first mouthpiece assembly, said cable assembly having a length that permits said first patient to view a display on said base unit while exhaling into said first mouthpiece assembly during a test;
- wherein said processor is used to obtain said first patient identification information from said first mouthpiece memory when said first mouthpiece assembly is connected to said base unit and said processor is used to obtain said second patient identification information from said second mouthpiece memory when said second mouthpiece assembly is connected to said base unit.

20. A system for obtaining information related to respiratory functions from at least one patient, comprising:
- a mouthpiece assembly that includes a mouthpiece device into which the patient exhales and a mouthpiece memory that stores identification information for a first patient, said mouthpiece assembly being located at one of: (i) a home of at least a first patient and (ii) a hospital; and
- a base unit located at said one of the home and the hospital and being joined to said mouthpiece assembly, said base unit including a processor for reading said first patient identification information from said mouthpiece memory and a base unit memory for storing said first patient identification information with respiratory-related data from the first patient, with said processor correlating said patient data with said first patient identification information when storing said first patient data.

21. A system, as claimed in claim 20, further including:
- a second mouthpiece assembly that includes a mouthpiece memory for storing identification information for a second patient different from the first patient and in which said second mouthpiece assembly is joined to said base unit after said first mouthpiece assembly is removed therefrom.

22. A system, as claimed in claim 20, further including:
- a docking station in communication with said mouthpiece assembly for use in downloading said first patient identification information to said mouthpiece memory.

23. A system for obtaining information related to respiratory functions from at least one patient, comprising:
- a mouthpiece assembly that includes a mouthpiece device into which the patient exhales, a flow board connected to said mouthpiece device, and a mouthpiece memory associated with said flow board that stores identification information for a first patient; and
- a base unit joined to said mouthpiece assembly and including a processor for reading said first patient identification information from said mouthpiece memory and a base unit memory for storing said first patient identification information with respiratory-related data from the first patient, with said processor correlating said patient data with said first patient identification information when storing said first patient data, said base unit including a display for displaying information related to symptoms of the first patient including at least one of the following: dyspnea, phlegm, shortness of breath, and wheezing.

24. A system for obtaining information related to respiratory functions from at least one patient, comprising:
- a mouthpiece assembly that includes a mouthpiece device into which the patient exhales, a flow board connected to said mouthpiece device, and a mouthpiece memory associated with said flow board that stores identification information for a first patient; and
- a base unit joined to said mouthpiece assembly and including a processor for reading said first patient identification information from said mouthpiece memory and a base unit memory for storing said first patient identification information with respiratory-related data from the first patient, with said processor correlating said patient data with said first patient identification information when storing said first patient data, said base unit including an input element that inputs at least one magnitude related to a first symptom, with said one magnitude related to a degree of the first symptom identified by the first patient.

25. A system for obtaining information related to respiratory functions from at least one patient, comprising:

a mouthpiece assembly that includes a mouthpiece device into which the patient exhales, a flow board connected to said mouthpiece device, and a mouthpiece memory associated with said flow board that stores identification information for a first patient; and a base unit joined to said mouthpiece assembly and including a processor for reading said first patient identification information from said mouthpiece memory and a base unit memory for storing said first patient identification information with respiratory-related data from the first patient, with said processor correlating said patient data with said first patient identification information when storing said first patient data, said base unit including a controler that stores in said base unit memory first patient data related to exhalation by the first patient using said mouthpiece assembly.

26. A system for obtaining information related to respiratory functions from at least one patient, comprising:

a mouthpiece assembly that includes a mouthpiece device into which the patient exhales, a flow board connected to said mouthpiece device, and a mouthpiece memory associated with said flow board that stores identification information for a first patient; and a base unit joined to said mouthpiece assembly and including a processor for reading said first patient identification information from said mouthpiece memory and a base unit memory for storing said first patient identification information with respiratory-related data from the first patient, with said processor correlating said patient data with said first patient identification information when storing said first patient data, said base unit including a display member and said mouthpiece assembly includes a cable assembly including a proximal connector, a cable member, and a distal connector, said proximal connector being disposed adjacent to said base unit, said distal connector being located at a distance from said display member of said base unit and said cable member being located intermediate of and connected to each of said proximal and distal connectors.

27. A system for obtaining information from at least one patient related to respiratory functions, comprising:

a mouthpiece assembly including a mouthpiece device into which a patient exhales and a mouthpiece memory for storing patient identification information;

a base unit operatively connected to said mouthpiece assembly and including a processor for processing patient data, a memory for storing patient data, and a display for displaying at least patient instructions; and a cable assembly operatively connected to said mouthpiece device, said cable assembly including a proximal connector located adjacent to said base unit, a distal connector located at a distance from said base unit, and a cable member interconnecting said proximal connector and said distal connector for carrying data between said mouthpiece device and said base unit, wherein said cable member has a length such that the patient is able to view said display when exhaling.

28. A system for obtaining information from at least one patient related to respiratory functions, comprising:

a mouthpiece assembly including a mouthpiece device into which a patient exhales;

a base unit operatively connected to said mouthpiece assembly and including a processor for processing patient data, a memory for storing patient data, and a display for displaying at least patient instructions; and a cable assembly operatively connected to said mouthpiece device, said cable assembly including a proximal connector located adjacent to said base unit, a distal connector located at a distance from said base unit, and a cable member interconnecting said proximal connector and said distal connector for carrying data between said mouthpiece device and said base unit, wherein said cable member has a length such that the patient is able to view said display when exhaling and said cable member has a length of at least 18 inches.

29. A system for obtaining information from at least one patient related to respiratory functions, comprising:

a mouthpiece assembly including a mouthpiece device into which a patient exhales;

a docking station that communicates with said mouthpiece assembly for use in downloading patient identification information thereto;

a base unit operatively connected to said mouthpiece assembly and including a processor for processing patient data, a memory for storing patient data, and a display for displaying at least patient instructions; and a cable assembly operatively connected to said mouthpiece device, said cable assembly including a proximal connector located adjacent to said base unit, a distal connector located at a distance from said base unit, and a cable member interconnecting said proximal connector and said distal connector for carrying data between said mouthpiece device and said base unit, wherein said cable member has a length such that the patient is able to view said display when exhaling.

* * * * *